(12) United States Patent
Zahiri et al.

(10) Patent No.: US 8,187,276 B1
(45) Date of Patent: May 29, 2012

(54) ODD ANGLE INTERNAL BONE FIXATION DEVICE FOR USE IN A TRANSVERSE FRACTURE OF A HUMERUS

(76) Inventors: Christopher A. Zahiri, Los Angeles, CA (US); Hormoz Zahiri, Los Angeles, CA (US)

( * ) Notice: Subject to any disclaimer, the term of this patent is extended or adjusted under 35 U.S.C. 154(b) by 782 days.

(21) Appl. No.: 11/527,927

(22) Filed: Sep. 26, 2006

(51) Int. Cl.
*A61B 17/76* (2006.01)

(52) U.S. Cl. .......................................................... 606/65

(58) Field of Classification Search ............. 606/65–68, 606/53, 280–289, 297, 62, 71, 105, 70, 63, 606/64; 403/362
See application file for complete search history.

(56) References Cited

U.S. PATENT DOCUMENTS

| | | | | |
|---|---|---|---|---|
| 2,612,159 A * | 9/1952 | Collison | ......................... | 606/67 |
| 4,379,451 A * | 4/1983 | Getscher | ......................... | 606/68 |
| 4,628,923 A * | 12/1986 | Medoff | ......................... | 606/65 |
| 4,776,330 A * | 10/1988 | Chapman et al. | ......................... | 606/64 |
| 5,041,116 A * | 8/1991 | Wilson | ......................... | 606/65 |
| 5,087,260 A * | 2/1992 | Fixel | ......................... | 606/65 |
| 5,462,547 A * | 10/1995 | Weigum | ......................... | 606/65 |
| 5,514,138 A * | 5/1996 | McCarthy | ......................... | 606/65 |
| 5,534,027 A * | 7/1996 | Hodorek | ......................... | 128/898 |
| 5,558,674 A * | 9/1996 | Heggeness et al. | ......................... | 606/278 |
| 5,569,251 A * | 10/1996 | Baker et al. | ......................... | 606/281 |
| 5,578,035 A * | 11/1996 | Lin | ......................... | 606/68 |
| 5,607,428 A * | 3/1997 | Lin | ......................... | 606/287 |
| 5,693,055 A * | 12/1997 | Zahiri et al. | ......................... | 606/305 |
| 5,810,821 A * | 9/1998 | Vandewalle | ......................... | 606/65 |
| 5,871,485 A * | 2/1999 | Rao et al. | ......................... | 606/65 |
| 5,973,223 A * | 10/1999 | Tellman et al. | ......................... | 606/65 |
| 5,976,139 A * | 11/1999 | Bramlet | ......................... | 606/66 |
| 6,270,499 B1 * | 8/2001 | Leu et al. | ......................... | 606/64 |
| 6,468,278 B1 * | 10/2002 | Muckter | ......................... | 606/291 |
| 6,562,042 B2 * | 5/2003 | Nelson | ......................... | 606/62 |
| 6,695,844 B2 * | 2/2004 | Bramlet et al. | ......................... | 606/66 |
| 2002/0049445 A1 * | 4/2002 | Hall et al. | ......................... | 606/69 |
| 2002/0128654 A1 * | 9/2002 | Steger et al. | ......................... | 606/69 |
| 2002/0143333 A1 * | 10/2002 | von Hoffmann et al. | ......................... | 606/67 |
| 2005/0010224 A1 * | 1/2005 | Watkins et al. | ......................... | 606/65 |
| 2005/0015131 A1 * | 1/2005 | Fourcault et al. | ......................... | 607/116 |
| 2005/0059971 A1 * | 3/2005 | Michelson | ......................... | 606/69 |
| 2005/0149025 A1 * | 7/2005 | Ferrante et al. | ......................... | 606/62 |
| 2005/0273105 A1 * | 12/2005 | Konieczynski et al. | ......................... | 606/69 |
| 2006/0217711 A1 * | 9/2006 | Stevens et al. | ......................... | 606/60 |
| 2007/0270847 A1 * | 11/2007 | Shaw | ......................... | 606/65 |

* cited by examiner

*Primary Examiner* — Eduardo C Robert
*Assistant Examiner* — Jerry Cumberledge
(74) *Attorney, Agent, or Firm* — Thomas I. Rozsa

(57) ABSTRACT

The present invention is an improved unique odd angle internal fixation device for both a transverse and longitudinal fracture located at the junction of the metaphysis and diaphysis of a long bone such as the proximal humerus. The improved odd angle internal fixation device includes an elongated lag screw and a rectangular shaped guide plate having multiple holes throughout the plate to host pins and screws and four tips on the front side of the plate. A lag screw with a cylindric head having a hexagonal cavity introduced through the diaphyseal segment of the fracture at three angles, 90, and 150 and 160 degrees, cross fixing the respective bone longitudinal and transverse fracture line and settling in the depth of the epiphysis. An additional locking screw is introduced on the top of the lag screw head to securely lock the lag screw after being settled into the epiphysis. The guide plate serves as a guide for the lag screw and allows the engagement of the head of the lag screw to the inner wall of its short barrel portion. The engagement would cause the guide plate which is attached to the barrel, to be compressed against the diaphyseal cortex as the lag screw advances deeper into the epiphysis at said three angles.

21 Claims, 5 Drawing Sheets

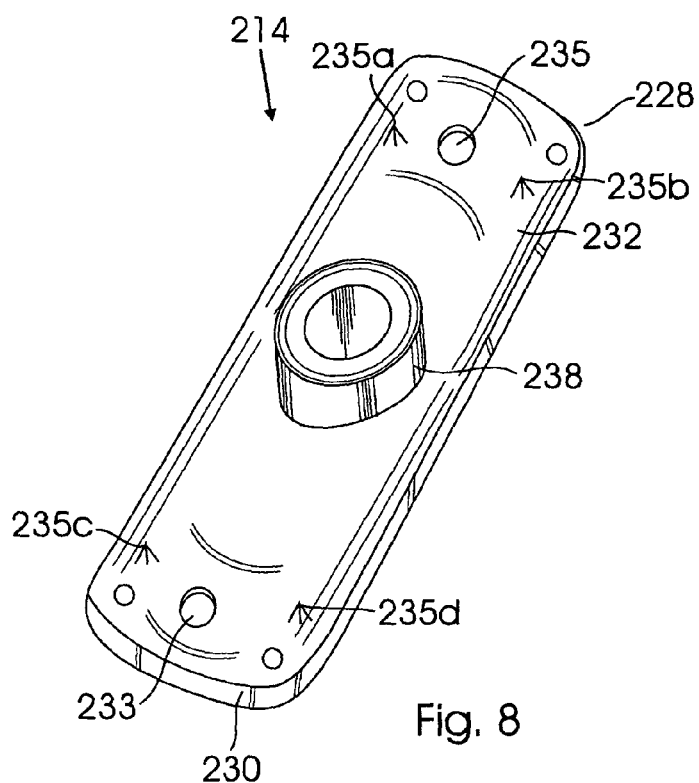
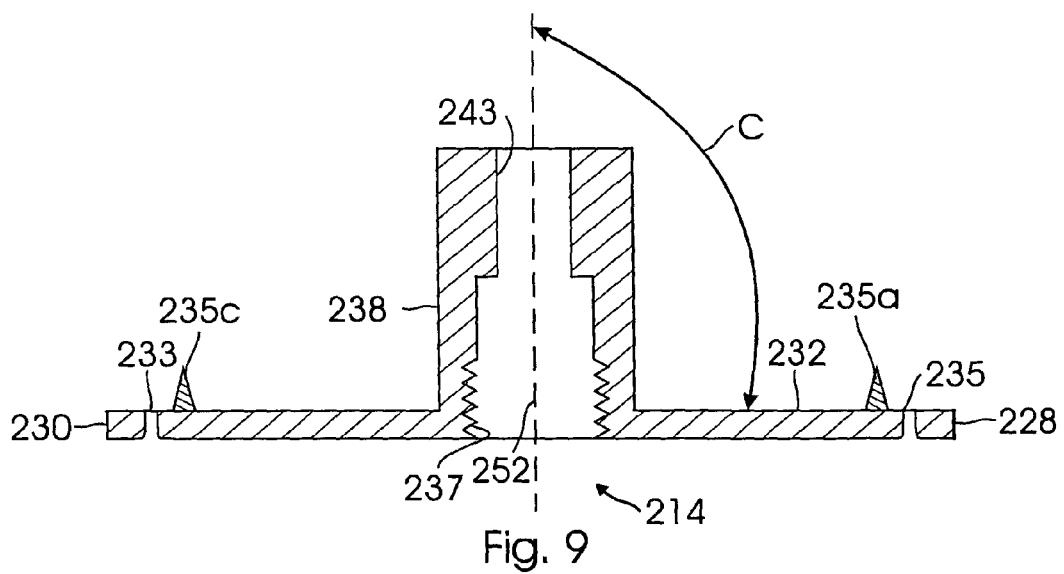
Fig. 8
Fig. 9

ODD ANGLE INTERNAL BONE FIXATION DEVICE FOR USE IN A TRANSVERSE FRACTURE OF A HUMERUS

BACKGROUND OF THE INVENTION

1. Field of the Invention

The present invention relates to the field of medical devices. More particularly, the present invention relates to the field of fixation devices for compressing bone fractures of a human being.

2. Description of the Prior Art

U.S. Pat. No. 5,693,055 by the same inventors discloses a unique odd angle internal fixation device for a transverse fracture located at the junction of the metaphysis and diaphysis of a long bone such as the proximal humerus. The device includes an elongated lag screw and a rectangular shaped guide plate. The lag screw is introduced through the diaphyseal segment of the fracture at an angle ranging approximately between 155° to 170°, cross fixing the bone fracture line and settling in the depth of the epiphysis. The guide plate serves as a guide for the lag screw and allows the engagement of the head of the lag screw to the inner wall of its short barrel portion. The engagement causes the guide plate which is attached to the barrel to be compressed against the diaphyseal cortex as the lag screw advances deeper into the epiphysis at an angle ranging approximately between 155 degrees to 170 degrees. The device provided with a lag screw and a guide plate which has an inclined short barrel portion integrally attached to the guide plate at an angle from above said range will cross fix a fracture line of the junction of the metaphysis and diaphysis, or cross fix the osteotomy site of the junction of the metaphysis and diaphysis or it can be used for joint fusion.

It will be appreciated that the U.S. Patent discloses the device which has a correct mechanism for fixing the bone transverse fracture. However it must also be appreciated that there are a number of areas where the structure of the device could be improved so as to fix both longitudinal and transverse fractures.

This prior art odd angle internal bone fixation device with the screw having a slotted top end from its proximal head does not create a user friendly condition for a surgeon. This is because surgeon can only tighten the lag screw when the position of the flat head of a screw driver used by the surgeon matches the position of the slotted top end of the lag screw. Therefore, the surgeon must redirect part of his attention to the position of the screw driver he is using, which could create problems if the surgeon must divert his attention from the medical issues of the surgical operation.

In addition, this prior art rectangular shaped guide plate of the device also does not create a user friendly condition for the surgeon since it is difficult for the surgeon to stabilize the plate at a position of the diaphsis cortex of the humerus determined by the surgeon, and in addition the plate is unstable in operation when the lag screw is pushed and turned to settle into the bone. An appropriate structural fixture designed for the plate is necessary to make it easily lock at a position of the diaphsis cortex and further keep it stable during operation when the lag screw is pushed and turned into the bone structure.

Another problem with the prior art device is that the screw which settles in the depth of the epiphysis after surgery could be loosened from its initial position if a patient performs excess movement of the body part where the fractured bone is located. To avoid such risk, the patient is advised to have a limited movement of the body part until the screw is fussed with the born structure, which could take a long time to happen. Obviously, this creates potential problems for the patient.

In addition, it is difficult for the surgeon to precisely follow a desired angle for driving the lag screw to settle into the bone without having a guide hole with the desired angle through a path that the lag screw is intended to drive through.

There is a significant need for a device which can be used to fix a longitudinal bone fracture in addition to its application to fix a transverse bone fracture, since longitudinal bone fractures also frequently occur.

SUMMARY OF THE INVENTION

The present invention is an improved unique odd angle internal fixation device for both a transverse and longitudinal fracture located at the junction of the metaphysis and diaphysis of a long bone such as the proximal humerus.

The improved odd angle internal fixation device includes an elongated lag screw and a rectangular shaped guide plate having multiple holes throughout the plate to host pins and screws and four tips on the front side of the plate. A lag screw with a cylindrical head having a hexagonal cavity is introduced through the diaphyseal segment of the fracture at three angles, 90 degrees, and 150 degrees or 160 degrees, cross fixing the respective bone longitudinal and transverse fracture line and settling in the depth of the epiphysis. An additional locking screw is introduced on the top of the lag screw head to securely lock the lag screw after being settled into the epiphysis. The guide plate serves as a guide for the lag screw and allows the engagement of the head of the lag screw with the inner wall of its short barrel portion. The engagement would cause the guide plate which is attached to the barrel to be compressed against the diaphyseal cortex as the lag screw advances deeper into the epiphysis at said three angles.

The improved odd angle internal fixation device further contains newly designed four pins and one or two additional screws through the plate as well as four tips on the front side of the guide plate. The pins are used to aid ib locating the plate at a position of the diaphsis cortex of the humerus, and are also used to stabilize the plate during a surgical operation when the lag screw is pressed and turned into the humerus. The pins are removed after the lag screw is settled inside of the epiphysis. The screws provide additional force to compress the plate to the cortex of the humerus in addition to the lag screw which provides a predominant contribution for compression of the plate. The four tips are also able to lock in the plate when they are pressed into the bone cortex after the lag screw is engaged into the depth of the epiphysis. The guide plate is further designed to be able to aid in making a guide hole at a desired angle so that the lag screw can be turned into the bone at the desired angle following the guide hole.

It has been discovered, according to the present invention, that if an odd angle internal fixation device is provided with a lag screw and a guide plate which has an inclined short barrel portion integrally attached to the guide plate at a degree angle of 150 degrees, or 160 degrees, then it will cross fix a transverse fracture line of the junction of the metaphysis and diaphysis, or cross fix the osteotomy site of the junction of the metaphysis and diaphysis or it can be used for joint fusion. With the addition of a 90 degree angle screw, it will cross fix a longitudinal fracture line located in the epiphysis portion of the bone.

It has further been discovered, according to the present invention, that if the lag screw has the hexagonal cavity on its top head, it will prove a user friendly condition to the surgeon to tighten the lag screw into the epiphysis during a surgical procedure.

It has also been discovered, according to the present invention, that if an additional locking screw is introduced on the top of the lag screw after it has settled inside of the epiphysis to securely lock the lag screw, it will provide stability of the lag screw inside of the bone immediately after a surgical operation even if there is excess movement of the body part where the fractured bone is located.

It has also further been discovered, according to the present invention, that the plate of the device can be prefixed on the cortex of the bone if additional pins are designed to temporarily lock in the plate by applying the pins to penetrate through the hole of the plate and partially into the inside of the bone segment so that it creates a user friendly condition for a surgeon to place the disclosed device at a desired location.

It has been discovered, according to the present invention, that one or two additional screws can be added into the plate, which will enhance tight contact from the plate to the cortex of the bone after the screws are turned into the bone structure. The plate will be further stabilized if tips are designed on the front side of the plate, which lock in the plate on the cortex after the plate is pressed to locate on the cortex of the bone.

It has additionally been discovered, according to the present invention, that with the aid of a newly designed hollow cylinder placed inside of the barrel of the guide plate, the guide plate can be further used to help make a guide hole on the bone for guiding the lag screw precisely to settle into the bone at a desired angle.

It is therefore an object of the present invention to provide an improved odd angle internal fixation device which can cross fix a transverse, or a longitudinal fracture line, osteotomy site or joint fusion at a respective angle of 150 degrees and 160 degrees, or 90 degrees.

It is a further object of the present invention to design a hexagonal cavity of the head of the lag screw to provide the surgeon with a user friendly condition to tight the screw into the epiphysis.

It is an additional object of the present invention to provide a guide plate which has additional fixation pins, screws, and tips which are specifically used to stabilize the guide plate against the bone cortex at a position for a surgical process before, during, and after the surgical operation when the lag screw is driven into the epiphysis.

It is an further additional object of the present invention to provide a locking screw on the top of the lag screw settled inside of the bone to stabilize the position of the lag screw immediately after surgery even in a situation where there is excess movement of the body part where the fractured bone is located.

It is an additional object of the present invention to provide a hollow cylindrical accessory, which can be placed inside of the barrel of the guide plate, so that the plate can be used to help make a guide hole at a desired angle for the lag screw wherein the lag screw can be driven along the guide hole to be precisely settled inside of the bone.

In the preferred embodiment of the present invention, a major point of uniqueness is having the odd angle internal fixation device which includes an elongated lag screw and a rectangular shaped guide plate which has a short barrel portion at an inclined angle of 90 degrees, 150 degrees, and 160 degrees. However, it should be appreciated that the present invention can also be utilized with a rectangular shaped guide plate which has a short barrel portion at an inclined angle in the range of from 90 to 170 degrees.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 8 is a top perspective view of the front surface of the rectangular shaped guide plate having a 90 degree angle shown in FIG. 6; and FIG. 9 is a cross-sectional view of still another embodiment of the present invention rectangular shaped guide plate, showing the short barrel portion at an angle of 90 degrees.

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
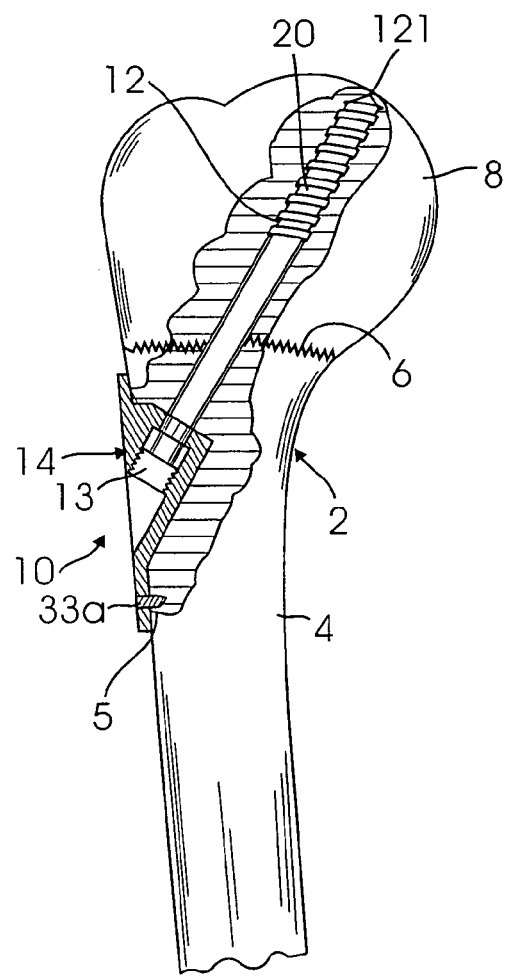
FIG. 1 is a side elevational view in partial cross-section of one of the embodiments of the present invention improved odd angle internal fixation device, showing the device fitted at two preferred angles of 150 degrees and 160 degrees to fix a transverse fracture, as it would be used, with portions of the diaphysis being cut away for illustrative purposes.

Referring to FIG. 1, there is shown at 10 one of the embodiments of the present invention improved odd angle internal fixation device, illustrating the device fitted as it would be used in a fracture of the diaphysis 2. The improved odd angle internal fixation device 10 includes an elongated lag screw 12, a plate 14, a locking screw 13, and an additional screw 33a introduced through the diaphyseal segment 4 of the fracture at an angle of 150 degrees or 170 degrees, cross fixing the transverse fracture line 6 and settling in the depth of the epiphysis 8.

Figure 2:
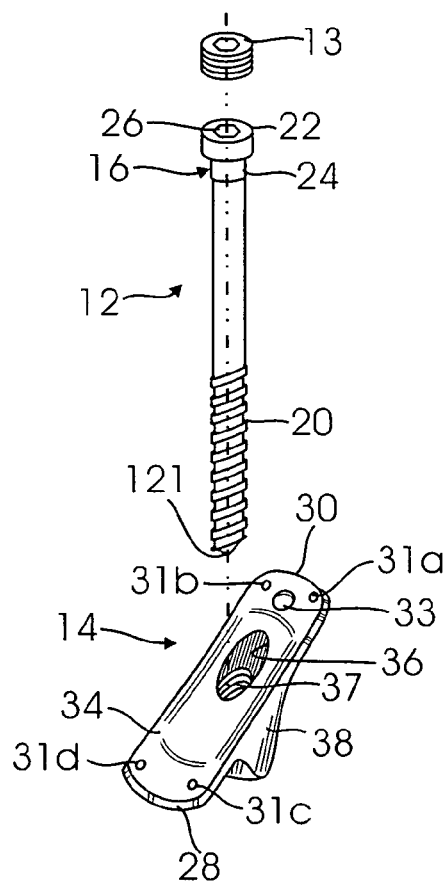
FIG. 2 is an enlarged exploded perspective view the present invention improved odd angle internal fixation device, shown in the embodiment of FIG. 1.

FIG. 2 shows an enlarged exploded perspective view of the present invention improved odd angle internal fixation device 10 which includes the locking screw 13, the elongated lag screw 12 and the generally rectangular shaped guide plate 14. Referring to FIGS. 1 and 2, the lag screw 12 has a proximal portion 16 and a distal threaded portion 20 with an end 121. The proximal portion 16 is provided with a proximal head 22 and a proximal cylinder 24. The proximal head 22 has a hexagonal cavity 26 which is provided to accommodate a driving tool, such as a hexagonal tip screwdriver to drive the lag screw 12 into the epiphysis 8. With the improvement applying the hexagonal structure, the present invention provides the surgeon a user friendly condition for driving the lag screw, so that the surgeon does not need to pay attention as to whether or not the position of the flat head of the screw driver matches that of the slotted top end of the lag screw disclosed in the prior U.S. Pat. No. 5,693,055. Therefore, the doctor can fully concentrate on the medical details of the surgical operation. This improvement is significant since it eliminates an interference factor to the surgeon during a surgical operation and enhances the assurance of the success of the surgery.

It will be appreciated that the cavity 26 is not limited to the hexagonal shape. The proximal head 22 can be manufactured with a cross head top end, so that a cross-headed screwdriver can drive the lag screw 12 into the diaphysis.

The lag screw 12 has different diameters. The diameter of the proximal cylinder 24 is the smallest diameter and is the same as the diameter of the thread depth of the distal threaded portion 20. The diameter of the proximal head 22 is the largest, which is larger than the diameter of the threads of the distal threaded portion 20.

Figure 3:
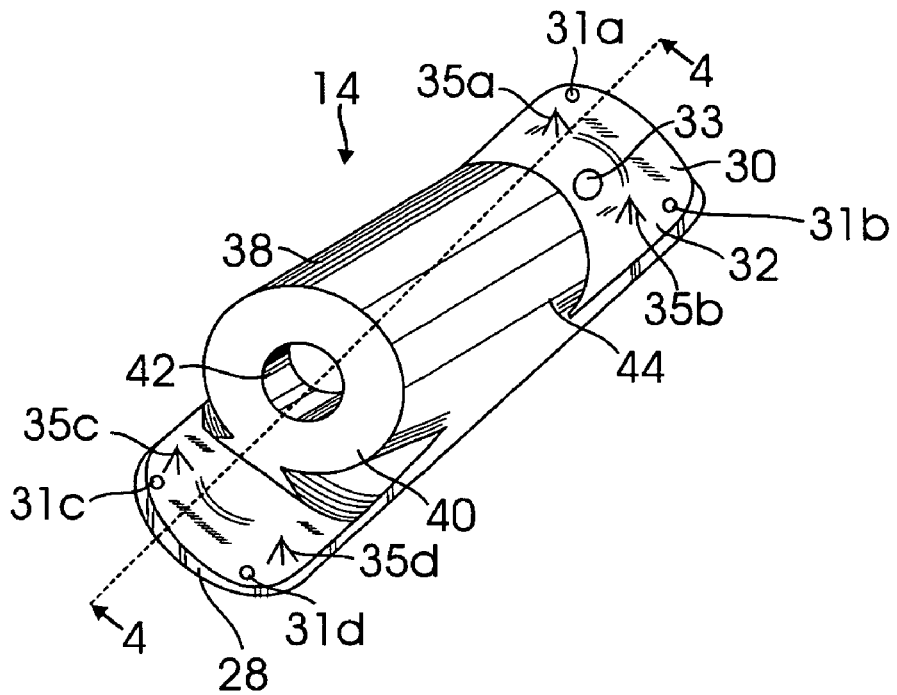
FIG. 3 is an enlarged top perspective view of the rectangular shaped guide plate with a guide angle of 150 degrees or 160 degrees.
Figure 4:
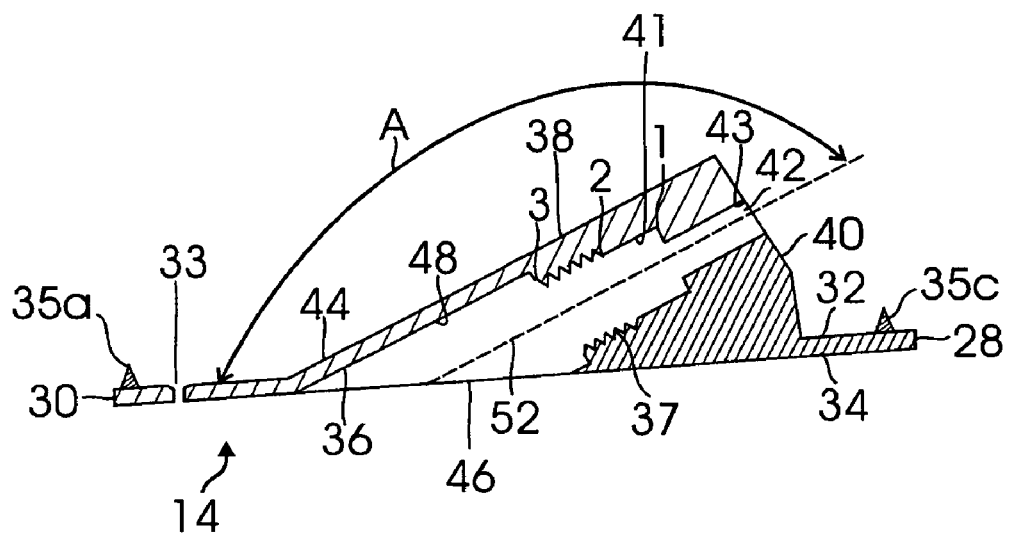
FIG. 4 is a cross-sectional view taken along line 4-4 of FIG. 3, showing the short barrel portion of the guide plate at an angle of 150 degrees.

FIG. 3 shows an enlarged top perspective view of the rectangular shaped guide plate 14. FIG. 4 shows a cross-sectional view of the guide plate 14. Referring to FIGS. 2, 3 and 4, the guide plate 14 has two opposite ends 28 and 30, a front side 32, a back side 34, and a bore 36, which contains a threaded portion 37 therethrough which is located off-center and adjacent to one end 30 of the guide plate 14. The two opposite ends 28 and 30 are generally linear with two round corner at both ends. The plate 14 is slightly curved on its transverse ends. As shown in FIG. 2, there is illustrated a convex backside 34 of the plate 14. As also shown in FIG. 3, the front side of the plate 14 is concave. With the aid of the curved structure, the plate 14 is able to better fit the diaphyseal segment of the humerus when the front side 32 of the plate is pressed to contact the cortex 5 shown in FIG. 1.

Referring to FIGS. 2 and 3, there is illustrated the guide plate 14 having four small holes 31a, 31b, 31c, and 31d respectively located at each corner of the rectangular plate and a medium size hole 33 located on the cental line of the plate close to the proximal end 44. All of the five holes are perpendicular through the plate. The plate further has four tips 35a, 35b, 35c, and 35d also respectively located close to each corner of the plate 14, but they are further away from the corners than the four small holes. The four tips are arranged perpendicular to the plane, wherein they extend from the back side 34 to the front side 32 of the plate 14. These four tips also serve to lock the plate when the plate is pressed to the diaphsis cortex of the humerus. It will be appreciated that these four tips could be located at other places on the front surface of the plate. It will further be appreciated that more or less tips could be used as long as they are able to lock the plate on the cortex. The hole 33 is designed to host an additional screw 33a to fix the plate 14 to the diaphsis cortex of the humerus.

The present invention improved odd angle internal bone fixation device provides a guide plate which is transversely curved, and can dissipate all the compression forces of the odd angle internal fixation device that are applied against the bone cortex, and practically reduce the forces to an easily tolerable level by the bone cortex. The repetitive normal use of the upper extremity after fixation cannot cause any failure by loosening of the device because the forces applied are well dissipated around the guide plate, and therefore the bone cortex remains healthy and intact. The guide plate is designed to serve as a very low profile fixation device palpable over the patient's extremity at the surgical site. The guide plate is far less prominent than the head of a screw, especially when used at an angle.

Referring to FIGS. 3 and 4, there is shown a short barrel portion 38 which is integrally attached to the guide plate 14. The short barrel portion 38 is a cylindrical hollow structure, having a distal end 40 with an opening 42, an opening side wall 43, an inner cylindrical wall 41, a threaded side wall portion 37, an inner side wall 48, and a proximal end 44 with an opposite opening 46. Further referring to FIG. 4, there is illustrated the threaded wall portion 37 which has a length defined between the second point 2 to a third point 3, which is slightly less than the height of the locking screw 13. The inner cylinder wall 41 has a length defined between the first point 1 and the second point 2, which is the same as the height of the proximal head 22 of the lag screw 12. The opening side wall 43 connected to the threaded wall 37 connected to the inner side wall 48 defines a passage 52 which extends from the distal end opening 42 to the proximal end opening 46, where the internal diameter of the opening side wall 43 is the least smallest, the inner side wall 48 the largest diameter, and the threaded wall 37 has the intermediate diameter. The proximal end 44 of the short barrel portion 38 is integrally attached to the front side 32 of the guide plate 14 at an inclined angle "A" of 150 degrees such that the proximal end opening 46 of the barrel portion 38 communicates with the bore 36 of the guide plate 14.

Figure 6:
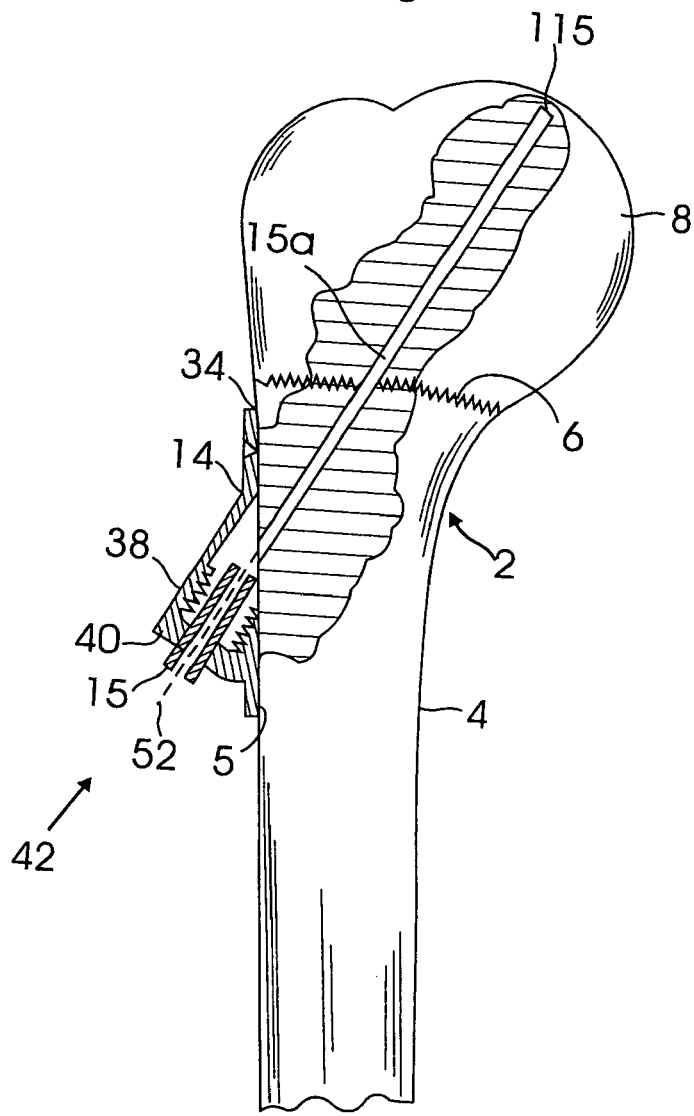
FIG. 6 is a side elevational view in partial cross-section to illustrate the plate with the access used for helping to draw a guide hole.

Referring to FIGS. 6, 2 and 4, the operation of the present invention improved odd angle internal fixation device 10 will be described. Before a surgical operation, an X-Ray analysis is performed, which determines a point in the longitudinal portion of the diaphyseal segment wherein a guide hole is going to be drilled, an angle of 140 degrees or 160 degrees is appropriate starting from the point, and extending for a distance from the point along the appropriate angle to cross the transverse fracture. After reading the results of the X-Ray analysis, the surgeon selects the improved odd angle internal bone fixation device wherein the guide plate contains the desired angle, and the lag screw has an appropriate length that is sufficient to cross the fracture line.

Referring to FIG. 6, there is illustrated a procedure to make a guide hole for the lag screw 12. In the procedure, the guide plate 14 is first placed at a location on the cortex, wherein the passage 52 is positioned at the point predetermined by x-Ray analysis. The plate 14 is further positioned so that its central longitudinal line is along to the longitudinal direction of the diaphyseal segment of the bone and the backside 34 of the plate 14 contacts the bone cortex. A drawing guide 15 is then slidably inserted into the passage 52 of the short barrel 38 from the opening 42 at the distal end 40 of the barrel 38, wherein the drawing guide 15 is a hollow cylinder having a central hole around its cylindrical rotational axis. The drawing guide 15 has a outside diameter which is slightly less than that of the opening 42. Referring to FIG. 6, the length of the drilling guide 15 is longer that of the barrel 38. Therefore, the drilling guide 15 has the same angle as that of the barrel 38 aligned against the diaphsis cortex of the humerus. Then a long drill shaft from a conventional drill is inserted into the hole of the drilling guide 15, wherein the diameter of the drill bit is sufficiently less than that of the hole, and a guide hole 15*a* is drilled following the desired angle wherein the end 115 of the hole 15*a* passes through the fracture line 6. After completion of the guide hole 15*a*, the guide plate 14 is removed. An additional hole with an appropriate diameter is then drew starting at the opening of the guide hole on the cortex following the direction of the desired angle and ending at a position, wherein the newly created hole can host the barrel 38 portion of the guide plate 14. The end point of the hole to host the barrel portion determines a new opening 215 (not show) of the guide hole 15*a*, along the direction of the desired angle.

Referring to FIGS. 1, 2, 4, and 6, the operation of the present invention improved odd angle internal fixation device 10 will be described. The short barrel portion 38 of the guide plate 14 is positioned within the hole formed through above described operation, wherein four tips 35*a*, 35*b*, 35*c*, and 35*d* on the front side 32 contact the diaphsis cortex of the humerus. Four small holes with their size less than the diameter of hole 31*a*, 31*b*, 31*c*, and 31*d* are drilled into the cortex. Then four pins are pressed throughout the hole 31*a*, 31*b*, 31*c*, and 31*d* in a direction from the back side 34 to the front side 32 of the plate 14 and pushed partially into the bone to lock the guide plate 14. The lag screw 12 is then slidably received within the passage 52 of the barrel portion 38 from the back side 34 of the guide plate 14, where the interior of the short barrel portion 38 is designed so that the lag screw 12 engages into the barrel portion 38 at three different diameters of the passage 52. The lag screw 12 is then threaded into the guide hole 15*a* to advance into the epiphysis 8 when its end 121 hits the opening 115 of the guide hole 15*a*. When the lag screw 12 is received within the short barrel portion 38, the diameter of the proximal shoulder flange 24 is slightly less than the internal diameter of the distal end opening 42 of the barrel portion 38 and provides a press fitted engagement thereon. The proximal head 22 of the lag screw 14 is slightly less than the diameter of the thread surface 37 of the short barrel portion 38 and provides a press fitted engagement thereon. This would create the desired precision for the engagement and provides the necessary mechanical advantage for utmost solid compression in the improved odd angle internal fixation device 10. In this situation, four tips on the front side 32 of the plate 14 will be pressed further into the bone cortex due to pressure force of the lag screw 12 engaged into the epiphysis 8, which results in additional force to stabilize the plate 14 onto the bone cortex, in addition to of the pressure force provided by the lag screw 12. It is understood that a perfect contact is reached between the concave front surface 32 of the plate 14 and the convex bone cortex in this operation.

Once the lag screw 12 is received within the barrel portion 38, the distal threaded portion 20 extends out of the barrel portion 38 and is introduced through the diaphyseal segment 4 of the fracture at angle "A", cross fixing the fracture line 6 and settling in the depth of the epiphysis 8.

In this operation, the specially designed guide plate 14 and the guide hole 15*a* serve to guide the elongated lag screw 12 and allow the engagement of the proximal head 22 of the lag screw 12 to the threaded wall 37 of the short barrel portion 38. The engagement would cause the guide plate 14 which is attached to the barrel portion 38, to be compressed against the diaphyseal cortex 5 as the lag screw 12 advances deeper into the epiphysis 8 at an angle of 150 degrees or 160 degrees.

After the lag screw 12 is settled inside of the epiphysis 8 the four pins are pulled out, and a medium size screw 33*a* is pressed and turned through the hole 33 of the plate 14 and into the bone diaphyseal segment. The screw 33*a* provides an additional force to press the guide plate 14 on the bone. After these processes, a locking screw 13 is introduced into the passage 52 of the barrel portion 38 from the opening 46 on the backside 34 of the guide plate 14, wherein the internal diameter of the passage 52 is sufficiently lager than the diameter of the locking screw 13. After the locking screw 13 reaches the first thread of threaded surface 37, the locking screw 13 is then turned and threaded forward to the head 22 of the lag screw 12. Finally the locking screw 13 is stopped when it contacts the top surface of the head 22 of the lag screw 22, which results in a secure lock of the lag screw 12 at its residing position inside of the epiphysis shown in FIG. 1.

Figure 5:
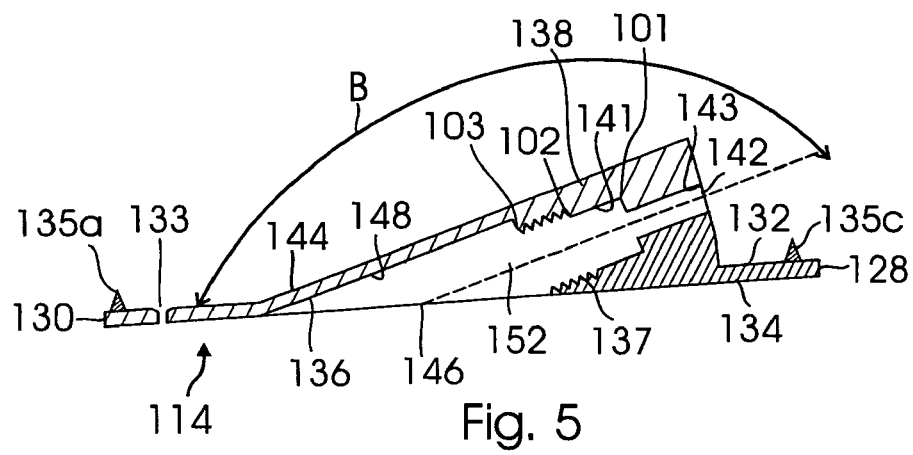
FIG. 5 is a cross-sectional view of another embodiment of the present invention rectangular shaped guide plate, showing the short barrel portion at an angle of 160 degrees.

Referring to FIG. 5, there is shown a cross-sectional view of another embodiment of the present invention improved odd angle internal fixation device. The parts are numbered correspondingly with 100 added to each number. This embodiment is identical to the first embodiment as previously described in FIGS. 1 through 4 except that the short barrel portion 138 of the guide plate 114 is now at an angle "B" which is at 160°. The same elongated lag screw is used with this embodiment, and since it assembles and functions the same as previously described, and the description thereof will not be repeated.

Figure 7:
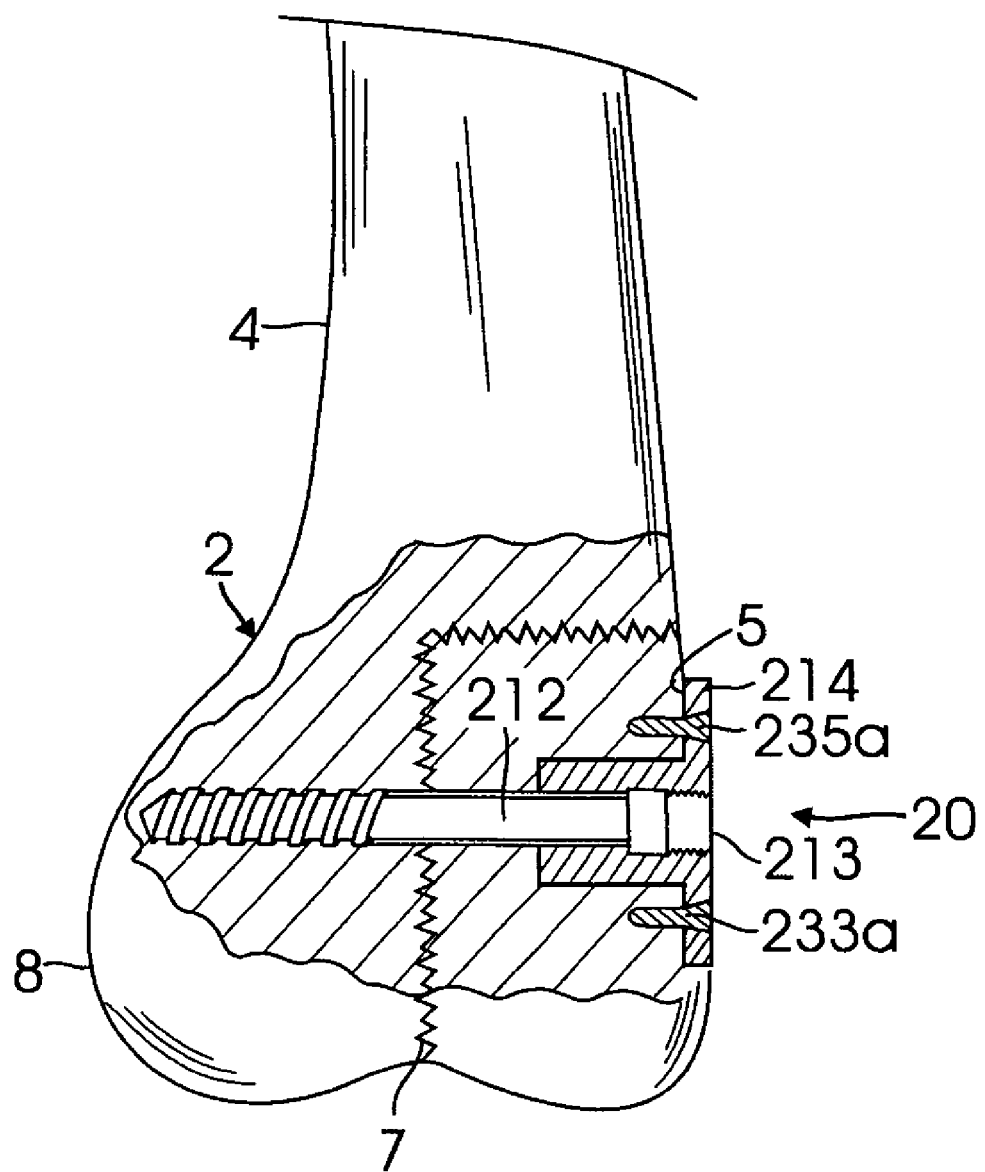
FIG. 7 is a side elevational view in partial cross-section side elevational view of another one of the embodiments of the present invention improved odd angle internal fixation device, showing the device fitted at 90 degree to fix a longitudinal fracture, as it would be used, with portions of the diaphysis being cut away for illustrative purposes.

Referring to FIG. 7, there is shown at 20 another one of the embodiments of the present invention improved odd angle internal fixation device, illustrating the device fitted as it would be used in the longitudinal fracture of the epiphysis 8. The improved odd angle internal fixation device 20 including an elongated lag screw 212, a plate 214, a locking screw 213, and two additional screws 233*a* an 235*a* is introduced through the epiphysic segment 8 of the fracture at an angle of 90 degrees, cross fixing the longitudinal fracture line 7 and settling in the depth of the epiphysis 8.

As illustrated FIG. 7, the device 20 is different from that of 10. The difference includes the barrel portion and two additional screws. Referring to FIG. 8, there is shown a short barrel portion 238 which is integrally attached to the front side 232 of the guide plate 214, wherein the short barrel portion 238 is perpendicularly located at the center of the rectangular plate 214. Two identical screw holes 233 and 235 are symmetrical relative to the center of the plate 214, and are respectively located adjacent to the two opposite ends 228 and 230 on the longitudinal central line of the plate 214. The same small holes and tips are also used with this embodiment, and since they assemble and function the same as previously described, and the description thereof will not be repeated.

Referring to FIG. 9, there is shown a cross-sectional view of still another embodiment of the present invention improved odd angle internal fixation device. This embodiment is identical to the first embodiment as previously described in FIGS. 1 through 4 except that the short barrel portion 238 of the guide plate 214 is now at an angle "C" which is approximately 90 degrees, perpendicular to the guide plate 214. In addition only the threaded wall 237 and opening wall 243 together defines a passage 252 of the barrel. The same elongated lag screw is used with this embodiment, and since it assembles and functions the same as previously described, the description thereof will not be repeated.

The present invention has many advantageous features, e.g., for the proximal humeral fracture, introduction of the internal fixation device into the bone is achieved through a small incision located below the attachment of the deltoid muscle where the humeral diaphysis is easily palpated. As a result, the need for deep dissection of the soft tissue in the proximity of the joint is eliminated. The improved odd angle internal fixation device can be manufactured in different sizes and used for similar fractures in a variety of joints. The improved odd angle internal fixation device may be used for solid fixation in osteotomies and in joint fusion. The improved odd angle internal fixation device can also be manufactured with other preferred angles ranging approximately between 90 degrees to 170 degrees and be used for a variety of fractures, fusion procedures and osteotomies. The present invention conforms to prior disclosed forms of manufacture, however, has the improved structure including a curved plate to better fit bone cortex, a locking screw to secure the lag screw, one or two additional screws for additional force to compress the plate, and four tips on the front side of the plate for enhancing stability of the plate, to achieve user friendly and security objectives.

Defined in detail, the present invention is an improved internal fixation device for use in a transverse fracture of the humerus, or in a longitudinal surgical head fracture of the epiphysis to cross fix the fracture line, the internal fixation device comprising: (a) a generally rectangular shaped guide plate for abutting against a diaphysis cortex of the humerus on one side of the fracture and having a front side, a back side and a bore containing threads therethrough located adjacent to one end of the guide plate, the guide plate being slightly transversely curved wherein the front side is concave and the back side convex, the guide plate having four small holes extending perpendicularly through the guide plate and respectively located adjacent each corner of the rectangular plate, the front side of the plate further having four tips extending perpendicularly to the plate wherein each tip extends transversely from the back side to the front side of the plate and each tip is respectively located adjacent each corner of the rectangular plate, the tips located further away from each corner than the holes, the plate having a the first option to be used exclusively for fixing the transverse fracture and having one additional medium size hole for hosting a screw located at a position along a longitudinal center line of the plate close to a proximal end of a barrel portion, the plate having a second option to be used exclusively for fixing the longitudinal fracture and having two additional medium size holes to host two screws symmetrically located relative to the center of the rectangular plate, at the centerline of the plate close to two ends of the plate; (b) a short barrel portion with a cylindrical hollow structure having the length of the barrel portion being sufficiently short so as not to cross the fracture line and also to rest a sufficient distance from the fracture line to leave a bone mass between the fracture line and a distal end of the short barrel portion, the short barrel portion having a first option to be used exclusively for fixing the transverse fracture to have a distal end with an opening, a proximal end with an opposite opening, an inner sidewall adjacent to the opposite opening, an opening wall adjacent to the distal end, an inner cylindrical wall adjacent to the opening in the wall, and a threaded wall adjacent to the inner side wall, the inner sidewall and the threaded wall and the inner cylindrical wall and the opening wall in series defining a passage extending from a proximal end opening to the distal end opening, the internal diameter of the distal end opening wall being the smallest and also being slightly bigger than that of the threaded teeth of the distal thread of the lag screw, the diameter of the inner wall being the largest, and diameter of the threaded wall being intermediate, the length of the threaded wall being slightly less than a height of a locking screw, the length of the inner cylinder wall is the same as the length of the proximal head of the lag screw, the short barrel portion having a second option to be used exclusively for fixing the longitudinal fracture to have a distal end with an opening and proximal end with an opposite opening, a threaded wall adjacent to the opposite opening, an opening wall adjacent to the distal end, and an inner cylinder wall in between the threaded wall and the opening wall, the threaded wall and the inner cylindrical wall and the opening wall defining a passage extending from the proximal end opening to the distal end opening, the internal diameter of the distal end opening wall being the smallest, the diameter of the threaded wall the largest, the length of the threaded wall being slightly less than a height of the locking screw, and a length of the inner cylindrical wall is the same as a height of the proximal head of the lag screw; (c) said proximal end of the barrel portion integrally attached to the front side of the guide plate, such that the passage is communicating with the bore of the guide plate, the short barrel portion used for adapting within the diaphysis cortex of the humerus such that the front side of the guide plate is placed against the diaphysis cortex of the humerus, the barrel portion attached to the plate at a preferred inclined angle, the inclined angle having the first option exclusively for fixing the transverse fracture to be either 150 degrees or 160 degrees, said inclined angle having the second option exclusively for fixing the longitudinal fracture to be 90 degrees; (d) an elongated lag screw for internally cross fixing the fracture line and settling in the depth of the epiphysis and having a distal threaded portion and a proximal portion, the proximal portion having a proximal cylinder and a proximal head having a hexagonal cavity with means for receiving a driving tool in its top end, the diameter of the proximal cylinder being smallest, the diameter of the thread teeth of the distal threaded portion being larger than that of the proximal cylinder, and the diameter of the proximal head being the largest; (e) said lag screw being slidably received within the passage of the barrel portion and extending out of the barrel portion following a pre-drilled mall guide hole for cross fixing the fracture line of the diaphysis cortex of the humerus with the distal threaded portion of the lag screw being located within the depth of the epiphysis, the proximal head of the lag screw being press-fitted within the distal end opening of the barrel portion such that the proximal head of the lag screw is contacting the inner cylinder wall of the short barrel portion and rests within the barrel portion for preventing the proximal head from extending out of the barrel portion when the guide plate is compressed against the diaphysis cortex of the humerus, and the guide plate adapted for being fixed to the diaphysis cortex of the humerus by the lag screw and dissipates all of the compression forces of the internal fixation device; (f) said guide plate is also compressed by one additional screw from the first option exclusively for fixing the transverse fracture, and two additional screws from the second option exclusively for fixing the longitudinal fracture; and (g) a locking screw being applied into the cylindrical hollow passage of the barrel through the proximal end opening, said locking screw being pressed and turned to contact the surface of the head of the lag screw for securely locking in the lag screw residing in the epiphysis; (h) whereby the guide plate dissipates all of the compression forces of the internal fixation device that are applied against the diaphysis cortex of the humerus, and thereby the diaphysis cortex of the humerus remains healthy and intact.

Defined more broadly, the present invention is an improved internal fixation device for use in a transverse surgical fracture of the humerus, or in a longitudinal surgical head fracture of the epiphysis to cross fix the fracture line, the internal fixation device comprising: (a) a generally rectangular shaped guide plate for abutting against the diaphysis cortex of the humerus on one side of the fracture, said guide plate being slightly curved wherein the front side is concave and back side convex, the guide plate having four small holes extending perpendicularly through the plate, and four tips extending perpendicularly to the plate, the holes and the tips respectively located adjacent each corner of the rectangular plate, the guide plate further comprising a short barrel portion with a cylindrical hollow structure having the length of the barrel portion being sufficiently short so as not to cross the fracture line and also to rest a sufficient distance from the fracture line to leave a bone mass between the fracture line and a distal end of the short barrel portion, the short barrel portion further comprising a proximal end integrally attached to the front side of the low profile guide plate, the short barrel portion used for adapting within the diaphysis cortex of the humerus such that the front side of the guide plate is placed against the diaphysis cortex of the humerus, the barrel portion attached to the guide plate at a preferred inclined angle; (b) an elongated lag screw for internally cross fixing the fracture line and settling in the depth of the epiphysis and having a distal threaded portion and a proximal portion, the proximal portion having a proximal cylinder and a proximal head having a cavity with means for receiving a driving tool in its top end; (c) said lag screw being slidably received within the passage of the barrel portion and extending out of the barrel portion following a pre-drilled small guide hole for cross fixing the fracture line of the diaphysis cortex of the humerus with the distal threaded portion of the lag screw being located within the depth of the epiphysis, and the guide plate adapted for being fixed to the diaphysis cortex of the humerus by the lag screw; and (d) a locking screw being applied into the cylindrical hollow passage of the barrel through the proximal end opening, said locking screw being pressed and turned to contact the surface of the head of the lag screw for securely locking in the lag screw which resides in the epiphysis; (e) whereby the guide plate dissipates all of the compression forces of the internal fixation device that are applied against the diaphysis cortex of the humerus, and thereby the diaphysis cortex of the humerus remains healthy and intact.

Defined even more broadly, the present invention is an improved internal fixation device for use in a transverse surgical fracture of the humerus, or in a longitudinal surgical head fracture of the epiphysis to cross fix the fracture line, the internal fixation device comprising: (a) a generally rectangular shaped guide plate for abutting against the diaphysis cortex of the humerus on one side of the fracture, the guide plate being curved, the guide plate having small holes extending perpendicularly through the plate and tips extending perpendicularly to the plate, said guide plate further comprising a short barrel portion with a cylindrical hollow structure having a length of the barrel portion being sufficiently short so as not to cross the fracture line and also to rest a sufficient distance from the fracture line to leave a bone mass between the fracture line and the distal end of the short barrel portion, said short barrel portion further comprising a proximal end integrally attached to the front side of the guide plate, said barrel portion attached to said guide plate at a preferred inclined angle; (b) a lag screw for internally cross fixing the fracture line having a distal threaded portion and a proximal portion, said lag screw being slidably received within the passage of the barrel portion and extending out of the barrel portion following a pre-drilled small guide hole for cross fixing the fracture line of the diaphysis cortex of the humerus, and when the guide plate is compressed against the humerus by the lag screw; and (c) a locking screw being applied to contact the surface of the head of the lag screw for securely locking the lag screw; (d) whereby the low profile guide plate dissipates all of the compression forces of the internal fixation device that are applied against the diaphysis cortex of the humerus, and thereby the diaphysis cortex of the humerus remains healthy and intact.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modifications in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. An improved internal fixation device for use in a transverse fracture of the humerus, the internal fixation device comprising:

a. a generally rectangular shaped guide plate capable of abutting against a diaphysis cortex of the humerus on one side of the fracture and having a front side, a back side and a bore containing threads therethrough located adjacent to one end of the guide plate, the guide plate being slightly transversely curved wherein the front side is concave and the back side convex, the guide plate having four small holes extending perpendicularly through the guide plate and respectively located adjacent each corner of the rectangular plate, the front side of the plate further having four tips extending perpendicularly to the plate wherein each tip extends transversely from the back side to the front side of the plate and each tip is respectively located adjacent each corner of the rectangular plate, the tips located further away from each corner than the holes, the plate used exclusively for fixing the transverse fracture and having one additional medium size hole for hosting a screw located at a position along a longitudinal center line of the plate close to a proximal end of a barrel portion;

b. a short barrel portion with a cylindrical hollow structure having the length of the barrel portion being sufficiently short so as not to cross the fracture line and also to rest a sufficient distance from the fracture line to leave a bone mass between the fracture line and a distal end of the short barrel portion, the short barrel portion used exclusively to be capable of fixing the transverse fracture to have a distal end with an opening, a proximal end with an opposite opening, an inner sidewall adjacent to the opposite opening, an opening wall adjacent to the distal end, an inner cylindrical wall adjacent to the opening, and a threaded wall adjacent to the inner sidewall, the inner sidewall and the threaded wall and the inner cylindrical wall and the opening wall in series defining a passage extending from the proximal end to the distal end, an internal diameter of the opening wall being the smallest and also being slightly bigger than that of threaded teeth of a distal threaded portion of an elongated solid lag screw, a diameter of the inner sidewall being the largest, and a diameter of the threaded wall being intermediate, a length of the threaded wall being slightly less than a height of a locking screw, a length of the inner cylindrical wall is the same as a length of a proximal head of the lag screw;

c. said proximal end of the barrel portion integrally attached to the front side of the guide plate, such that the passage is communicating with the bore of the guide plate, the short barrel portion used for adapting within the diaphysis cortex of the humerus such that the front side of the guide plate is placed against the diaphysis cortex of the humerus, the barrel portion attached to the plate at a preferred inclined angle, the inclined angle having the first option exclusively for fixing the transverse fracture to be either 150 degrees or 160 degrees;

d. said elongated solid lag screw capable of internally cross fixing the fracture line and settling in the depth of the epiphysis and having the distal threaded portion and a proximal portion, the proximal portion having a proximal cylinder and the proximal head having a hexagonal cavity with means for receiving a driving tool in said cavity, a diameter of the proximal cylinder being smallest, a diameter of threaded teeth of the distal threaded portion being larger than that of the proximal cylinder, and a diameter of the proximal head being the largest;

e. said lag screw being slidably received within the passage of the barrel portion and extending out of the barrel portion following a pre-drilled mall guide hole capable of cross fixing the fracture line of the diaphysis cortex of the humerus with the distal threaded portion of the lag screw being located within the depth of the epiphysis, the proximal head of the lag screw being press-fitted within the distal end opening of the barrel portion such that the proximal head of the lag screw is contacting the inner cylinder wall of the short barrel portion and rests within the barrel portion for preventing the proximal head from extending out of the barrel portion when the guide plate is compressed against the diaphysis cortex of the humerus, and the guide plate adapted to be capable of being fixed to the diaphysis cortex of the humerus by the lag screw and dissipates all of the compression forces of the internal fixation device; and f. said locking screw being applied into the cylindrical hollow structure of the barrel through the proximal end opening, said locking screw being pressed and turned to contact the surface of the proximal head of the lag screw for securely locking in the lag screw residing in the epiphysis;

g. whereby the guide plate dissipates all of the compression forces of the internal fixation device that are applied against the diaphysis cortex of the humerus, and thereby the diaphysis cortex of the humerus remains healthy and intact.

2. An improved internal fixation device for use in a transverse surgical fracture of the humerus, the internal fixation device comprising:

a. a generally rectangular shaped guide plate capable of abutting against the diaphysis cortex of the humerus on one side of the fracture, said guide plate being slightly curved wherein a front side is transversely concave and a back side is transversely convex, with the front side and back side being linear in the longitudinal direction, the guide plate having four small holes respectively located adjacent each corner of the plate and capable of positioning the device and four tips extending perpendicularly to the plate, the medium sized hole located adjacent one end of the guide plate and the tips respectively located adjacent each corner of the rectangular plate, the guide plate further comprising a short barrel portion with a cylindrical hollow structure having a length of the barrel portion being sufficiently short so as not to cross the fracture line and also to rest a sufficient distance from the fracture line to leave a bone mass between the fracture line and a distal end of the short barrel portion, the short barrel portion further comprising a proximal end integrally attached to the front side of the profile guide plate, the short barrel portion capable of adapting within the diaphysis cortex of the humerus such that the front side of the guide plate is placed against the diaphysis cortex of the humerus, the barrel portion attached to the guide plate at a preferred inclined angle;

b. an elongated solid lag screw capable of internally cross fixing the fracture line and settling in a depth of the epiphysis and having a distal threaded portion and a proximal portion, the proximal portion having a proximal cylinder and a proximal head having a cavity with means for receiving a driving tool in the cavity;

c. said lag screw being slidably and rotatably received within a cylindrical hollow passage of the barrel portion and extending out of the barrel portion following a pre-drilled small guide hole to provide a rotating and sliding forward movement relative to the guide plate to be capable of cross fixing the fracture line of the diaphysis cortex of the humerus with the distal threaded portion of the lag screw being located within a depth of the epiphysis, and the guide plate adapted to be capable of being fixed to the diaphysis cortex of the humerus by the lag screw, wherein the four tips are capable of penetrating through the cortex of the humerus to provide additional affixing forces to stabilize the device; and d. a locking screw being applied into the cylindrical hollow passage of the barrel through a proximal end opening, said locking screw being pressed and turned to contact an entire portion of the top surface of the proximal head of the lag screw capable of securely locking in the lag screw which resides in the epiphysis;

e. whereby the guide plate dissipates all compression forces of the internal fixation device that are applied against the diaphysis cortex of the humerus, and thereby the diaphysis cortex of the humerus remains healthy and intact.

3. The improved fixation device in accordance with claim 2 wherein said short barrel portion capable of fixing the transverse fracture and has a distal end with an opening, a proximal end with an opposite opening, an inner sidewall adjacent to the opposite opening, an opening wall adjacent to the distal end, and a threaded wall adjacent to the inner sidewall, and an inner cylindrical wall adjacent to the opening wall.

4. The improved fixation device in accordance with claim 2 wherein said inclined angle capable of fixing the transverse fracture to be either 150 degrees or 160 degrees.

5. The improved fixation device in accordance with claim 2 wherein said means for accommodating a driving tool is a cross cavity within the top of said proximal head.

6. The improved fixation device in accordance with claim 2, wherein a top of the lag screw further comprises means capable of accommodating a driving tool which is a hexagonal cavity within a top of the proximal portion.

7. An improved internal fixation device for use in a transverse surgical fracture of the humerus, comprising:

a. a generally rectangular shaped guide plate curved in a transverse direction and linear in a longitudinal direction and capable of abutting against a diaphysis cortex of the humerus on one side of the fracture, the guide plate having a medium sized hole extending perpendicularly through the plate and tips extending perpendicularly to the plate, said guide plate further comprising a short barrel portion with a cylindrical hollow structure having a length of the barrel portion being sufficiently short so as not to cross the fracture line and also to rest a sufficient distance from the fracture line to leave a bone mass between the fracture line and the distal end of the short barrel portion, said short barrel portion further comprising a proximal end which is integrally affixed to the front side of the guide plate and positioned at a fixed distance from said medium sized hole, said barrel portion integrally affixed to said guide plate at a preferred inclined angle;

b. a solid lag screw for internally cross fixing the fracture line having a distal threaded portion and a proximal portion with a head, said lag screw being slidably and rotatably received within a passage of the barrel portion and extending out of the barrel portion following a predrilled small guide hole to provide a rotating and sliding forward movement relative to said guide plate to cross fix the fracture line of the diaphysis cortex of the humerus, so that the guide plate is compressed against the diaphysis cortex of the humerus by the lag screw, wherein the tips are capable of penetrating through the cortex of the humerus to provide additional affixation forces to stabilize the device; and c. a locking screw being applied to contact an entire top surface of the head of the lag screw for securely locking the lag screw;

d. whereby the low profile guide plate dissipates all of the compression forces of the internal fixation device that are applied against the diaphysis cortex of the humerus, and thereby the diaphysis cortex of the humerus remains healthy and intact.

8. The improved fixation device in accordance with claim 7 wherein said plate for fixing the transverse fracture has one medium sized hole, and a screw is threaded to be capable of penetrating through the medium sized hole of the guide plate and further to be capable of penetrating through the disphysis cortex of the humerus for providing additional fixation of the guide plate.

9. The improved fixation device in accordance with claim 7 wherein said short barrel portion capable of fixing the transverse fracture has an inner sidewall adjacent to an opposite opening, an opening wall adjacent to a distal end, and an inner cylinder wall and a threaded wall in between.

10. The improved fixation device in accordance with claim 7 wherein said inclined angle capable of fixing the transverse fracture is either 150 degrees or 160 degrees.

11. The improved fixation device in accordance with claim 7 wherein the top of the lag screw further comprises means for accommodating a driving tool which is a cross cavity within the top of said proximal head.

12. The improved fixation device in accordance with claim 7 wherein the top of the lag screw further comprises means for accommodating a driving tool which is a hexagonal cavity within the top of said proximal head.

13. The improved fixation device in accordance with claim 7, further comprising: a screw is threaded to be capable of penetrating through the medium sized hole of the guide plate and further capable of penetrating through the disphysis cortex of the humerus for providing additional fixation of the guide plate.

14. The improved fixation device in accordance with claim 7, further comprising four small sized holes respectively located adjacent each corner of the plate capable of providing assistance for positioning the device.

15. An improved internal fixation device for using to fix a transverse surgical fracture of the humerus, comprising:

a. a guide plate curved in a transverse direction and linear in a longitudinal direction and capable of abutting against a diaphysis cortex of the humerus on one side of the fracture, the guide plate having tips extending perpendicularly to the plate and a medium sized hole capable of fixing said guide plate to said diaphysis cortex, said guide plate further comprising a short hollow barrel portion having a length being sufficiently short so that said short hollow barrel portion does not cross the fracture, said hollow short barrel portion is integrally affixed to a front side of said guide plate with a preferred inclined angle and positioned at a fixed distance from said medium sized hole;

b. a solid lag screw capable of internally cross fixing the fracture line having a distal threaded portion and a proximal portion, said lag screw being rotatably and slidably received by said short hollow barrel portion and extending out of the barrel portion from a rotating and sliding forward movement relative to said guide plate to be capable of cross fixing the fracture line of the diaphysis cortex of the humerus, which causes said guide plate that is compressed to be affixed to the diaphysis cortex of the humerus, wherein the tips are capable of penetrating through the cortex of the humerus to provide additional affixation forces to stabilize the device; and c. whereby said guide plate dissipates all of compression forces of said internal fixation device that are applied against said diaphysis cortex of the humerus, and thereby said diaphysis cortex of the humerus remains healthy and intact.

16. The improved fixation device in accordance with claim 15, wherein the short barrel portion capable of fixing the transverse fracture has a passage having an inner sidewall adjacent to an opposite opening, an opening wall adjacent to a distal end, and an inner cylindrical wall and a threaded wall in between.

17. The improved fixation device in accordance with claim 15, wherein said inclined angle capable of fixing the transverse fracture is either 150 degrees or 160 degrees.

18. The improved fixation device in accordance with claim 15, wherein a top of the lag screw further comprises means for accommodating a driving tool which is a cross cavity within a top of the proximal portion.

19. The improved fixation device in accordance with claim 15, wherein a top of the lag screw further comprises means for accommodating a driving tool which is a hexagonal cavity within a top of the proximal portion.

20. The improved fixation device in accordance with claim 15, further comprising: a screw is threaded to be capable of penetrating through the medium sized hole of the guide plate and further be capable of penetrating through the disphysis cortex of the humerus for providing additional fixation of the guide plate.

21. The improved fixation device in accordance with claim 15, further comprising four small sized holes respectively located adjacent each corner of the plate capable of providing assistance for positioning the device.

\* \* \* \* \*